(12) United States Patent
Fandrick et al.

(10) Patent No.: US 8,916,701 B2
(45) Date of Patent: Dec. 23, 2014

(54) METHODS OF MAKING DIASTEREOMERIC ORGANIC COMPOUNDS

(75) Inventors: Daniel Robert Fandrick, Danbury, CT (US); Zhi-Hui Lu, Newtown, CT (US); Diana Reeves, New Milford, CT (US); Jonathan Reeves, New Milford, CT (US); Chris Hugh Senanayake, Brookfield, CT (US); Jinhua Jeff Song, Hopewell Junction, NY (US); Yongda Zhang, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/921,145

(22) PCT Filed: Dec. 15, 2011

(86) PCT No.: PCT/US2011/065013
§ 371 (c)(1),
(2), (4) Date: Jan. 28, 2014

(87) PCT Pub. No.: WO2012/087720
PCT Pub. Date: Jun. 28, 2012

(65) Prior Publication Data
US 2014/0135493 A1   May 15, 2014

Related U.S. Application Data

(60) Provisional application No. 61/528,321, filed on Aug. 29, 2011, provisional application No. 61/424,834, filed on Dec. 20, 2010.

(51) Int. Cl.
C07D 413/10    (2006.01)
C07D 265/10    (2006.01)
C07D 213/64    (2006.01)

(52) U.S. Cl.
USPC .............................................. 544/97; 544/96

(58) Field of Classification Search
CPC ... C07D 413/10; C07D 265/10; C07D 213/64
USPC ........................................................ 544/96, 97
See application file for complete search history.

(56) References Cited

FOREIGN PATENT DOCUMENTS

WO   2010089303 A1   8/2010

OTHER PUBLICATIONS

International Search Report and Written Opinion for PCT/US2011/065013 mailed Mar. 7, 2012.

*Primary Examiner* — Kahsay Habte
(74) *Attorney, Agent, or Firm* — Michael P. Morris; David L. Kershner

(57) ABSTRACT

Disclosed is a process for making diastereomeric compound of the formula (I):

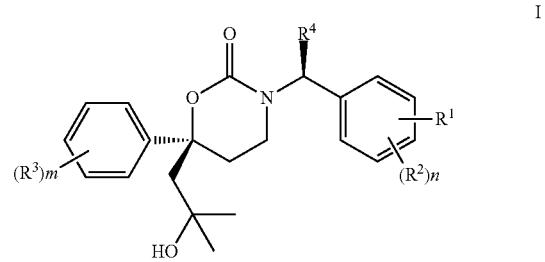

wherein m, n and $R^1$ to $R^4$ are as defined herein. The process of the invention provides the compound of formula (I) in high yield and substantially free of the corresponding diastereomers. The compounds of formula (I) prepared by the process of the invention are useful for making pharmaceutically active compounds such as 11-β-hydroxysteroid hydrogenase type 1 (11-β-HSD1) inhibitors.

6 Claims, No Drawings

METHODS OF MAKING DIASTEREOMERIC ORGANIC COMPOUNDS

This application relates to methods of making diastereomers of 1,3-disubstituted oxazinan-2-ones. The process of the invention provides the diastereomers in high yield and substantially free of the corresponding enantiomers. The compounds prepared by the process of the invention can be used to prepare pharmaceutically active compounds such as 11-β-hydroxysteroid hydrogenase type 1 (11-β-HSD1) inhibitors.

BACKGROUND OF THE INVENTION 1,3-disubstituted derivatives of oxazinan-2-ones are reportedly useful as inhibitors of 11-β-hydroxysteroid hydrogenase type 1 ("11-β-HSD1") and for treatment of disorders associated 11β-HSD1 activity including, for example, diabetes mellitus (e.g., type II diabetes), obesity, symptoms of metabolic syndrome, glucose intolerance, hyperglycemica (see, e.g., WO/2009/134400).

The oxazinan-2-one 11-β-HSD1 inhibitors can be prepared, for example, by methods described in WO/2009/134400 and WO/2010/010150. In one method, a compound of formula (A) is allowed to react with an appropriate Grignard reagent RMgBr to provide the oxazinan-2-one 11-β-HSD1 inhibitor of formula (B) as depicted below:

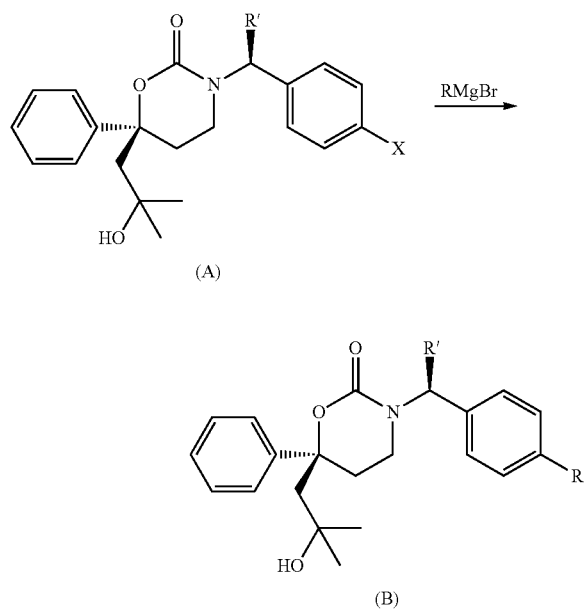

However, the above method (and other known methods) present challenges for large-scale preparations. Additionally, compounds of formula (A) and formula (B) prepared by the known methods often contain a substantial amount of impurities (e.g., stereoisomers, structural isomers, and/or reagents). Thus, there is a need for improved processes for making oxazinan-2-one 11-β-HSD1 inhibitors which are more amenable to large-scale production and provide a more pure form of the diastereomeric product.

BRIEF SUMMARY OF THE INVENTION

In one embodiment, the invention relates to a method of making the compound of formula (I):

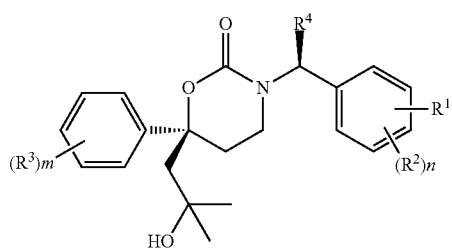

comprising allowing a compound of formula (II):

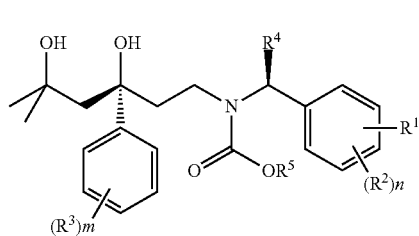

to react in the presence of base to form the compound of formula (I), wherein:

m and n are each independently 0, 1 or 2;

$R^1$ is a leaving group selected from chloro, bromo, iodo, methoxy, arylsulfonyloxy and trifluoromethanesulfonyloxy; or $R^1$ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing $R^1$ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —($C_1$-$C_6$)alkyl, —O($C_1$-$C_6$)alkyl, and —($C_3$-$C_6$)cycloalkyl; and wherein substituents for ring nitrogen atoms of said heterocyclic rings, when present, are selected from —($C_1$-$C_6$)alkyl and —($C_3$-$C_6$)cycloalkyl;

each $R^2$ and $R^3$ is independently selected from —($C_1$-$C_6$)alkyl, —O($C_1$-$C_6$)alkyl, and —($C_3$-$C_6$)cycloalkyl; wherein each of the —($C_1$-$C_6$)alkyl, —O($C_1$-$C_6$)alkyl, and —($C_3$-$C_6$)cycloalkyl of said $R^2$ and $R^3$ is optionally independently substituted with one to three $R^6$ groups;

$R^4$ is selected from —($C_1$-$C_6$)alkyl and —($C_3$-$C_6$)cycloalkyl; wherein the —($C_1$-$C_6$)alkyl and —($C_3$-$C_6$)cycloalkyl of said $R^4$ is optionally substituted with one to three $R^6$ groups;

$R^5$ is selected from —($C_1$-$C_6$)alkyl, —($C_3$-$C_6$)cycloalkyl, and phenyl; and each $R^6$ is independently selected from halo, —($C_1$-$C_6$)alkyl, —O($C_1$-$C_6$)alkyl, and —($C_3$-$C_6$)cycloalkyl.

In another embodiment, the invention relates to a method of making the compound of formula (I), wherein $R^1$ is bromo; and $R^4$ is —($C_1$-$C_6$)alkyl.

In another embodiment, the invention relates to a method of making the compound of formula (I), wherein m and n are each 0.

In another embodiment, the invention relates to a method of making the compound of formula (I) according to any of the embodiments above, wherein $R^4$ is methyl.

In another embodiment, the invention relates to a method of making the compound of formula (I) according to any of the embodiments above, wherein $R^5$ is phenyl.

In another embodiment, the invention relates to a method of making the compound of formula (I) according to the broadest embodiment above, wherein $R^1$ is bromo; $R^4$ is —$(C_1$-$C_6)$alkyl; $R^5$ is phenyl; and m and n are each 0.

In another embodiment, the invention relates to a method of making the compound of formula (I) according to the embodiment immediately above, wherein $R^4$ is methyl.

In another embodiment, the invention relates to a method of making the compound of formula (I) as described in the broadest embodiment above, wherein $R^1$ is oxodihydropyrid-4-yl; and wherein said nitrogen atom of said oxodihydropyrid-4-yl is substituted by methyl or cyclohexyl.

In another embodiment, the invention relates to a method of making the compound of formula (I) as described in the embodiment immediately above, wherein $R^1$ is oxodihydropyrid-4-yl and wherein said nitrogen atom of said oxodihydropyrid-4-yl is substituted by methyl or cyclohexyl; $R^4$ is methyl; and m and n are each 0.

In another embodiment, the invention relates to a method of making the compound of formula (I) according to any of the embodiments described above, wherein the base is selected from aqueous sodium hydroxide, aqueous potassium hydroxide and a mixture thereof.

In another embodiment, the invention relates to a method of making the compound of formula (I) according to any of the embodiments described above, further comprising an aprotic organic solvent that is miscible with water.

In another embodiment, the invention relates to a method of making the compound of formula (I) according to the embodiment described immediately above, wherein the aprotic organic solvent is N-methylpyrrolidone.

The invention also relates to methods of making the compound of formula (II):

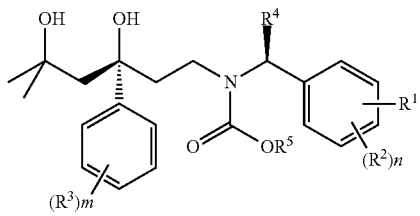

II comprising allowing a compound of formula (IV),

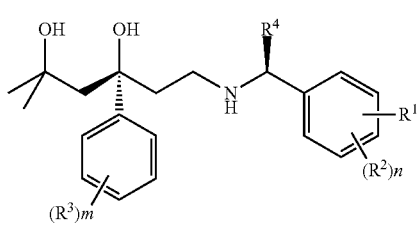

IV to react with a compound of formula (V):

$$R^5\text{—O—C(O)—}R^7$$

V to provide the compound of formula (II), wherein
m and n are each independently 0, 1 or 2;
$R^1$ is a leaving group selected from chloro, bromo, iodo, methoxy, arylsulfonyloxy and trifluoromethanesulfonyloxy; or
$R^1$ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing $R^1$ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —$(C_1$-$C_6)$alkyl, —$O(C_1$-$C_6)$alkyl, and —$(C_3$-$C_6)$cycloalkyl; and wherein substituents for ring nitrogen atoms of said heterocyclic rings, when present, are selected from —$(C_1$-$C_6)$alkyl and —$(C_3$-$C_6)$cycloalkyl;
each $R^2$ and $R^3$ is independently selected from —$(C_1$-$C_6)$alkyl, —$O(C_1$-$C_6)$alkyl, and —$(C_3$-$C_6)$cycloalkyl; wherein each of the —$(C_1$-$C_6)$alkyl, —$O(C_1$-$C_6)$alkyl, and —$(C_3$-$C_6)$cycloalkyl of said $R^2$ and $R^3$ is optionally independently substituted with one to three $R^6$ groups;
$R^4$ is selected from —$(C_1$-$C_6)$alkyl and —$(C_3$-$C_6)$cycloalkyl; wherein the —$(C_1$-$C_6)$alkyl and —$(C_3$-$C_6)$cycloalkyl of said $R^4$ is optionally substituted with one to three $R^6$ groups;
$R^5$ is selected from —$(C_1$-$C_6)$alkyl, —$(C_3$-$C_6)$cycloalkyl, and phenyl;
each $R^6$ is independently selected from halo, —$(C_1$-$C_6)$alkyl, —$O(C_1$-$C_6)$alkyl, and —$(C_3$-$C_6)$cycloalkyl; and
$R^7$ is selected from chloro, iodo, and bromo.

In another embodiment, the invention relates to a method of making the compound of formula (II), wherein $R^1$ is bromo; and $R^4$ is —$(C_1$-$C_6)$alkyl.

In another embodiment, the invention relates to a method of making the compound of formula (II), wherein m and n are each 0.

In another embodiment, the invention relates to a method of making the compound of formula (II), according to any of the embodiments above, wherein $R^4$ is methyl.

In another embodiment, the invention relates to a method of making the compound of formula (II), according to any of the embodiments above wherein $R^5$ is phenyl.

In another embodiment, the invention relates to a method of making the compound of formula (II) according to any of the embodiments, above wherein $R^7$ is chloro.

In another embodiment, the invention relates to a method of making the compound of formula (II) according to the broadest embodiment above, wherein $R^1$ is bromo; $R^4$ is —$(C_1$-$C_6)$alkyl; $R^5$ is phenyl; $R^7$ is chloro; and m and n are each 0.

In another embodiment, the invention relates to a method of making the compound of formula (II) according to the embodiment immediately above, wherein $R^4$ is methyl.

In another embodiment, the invention relates to a method of making the compound of formula (II) as described in the broadest embodiment above, wherein $R^1$ is oxodihydropyrid-4-yl; and wherein said nitrogen atom of said oxodihydropyrid-4-yl is substituted by methyl or cyclohexyl.

In another embodiment, the invention relates to a method of making the compound of formula (II) as described in the embodiment immediately above, wherein $R^1$ is oxodihydropyrid-4-yl and wherein said nitrogen atom of said oxodihydropyrid-4-yl is substituted by methyl or cyclohexyl; R⁴ is methyl; and m and n are each 0.

In another embodiment, the invention relates to a method of making the compound of formula (II) according to the two embodiments immediately above, wherein R⁵ is phenyl and R⁷ is chloro.

The invention also relates to methods of making the compound of formula (IV):

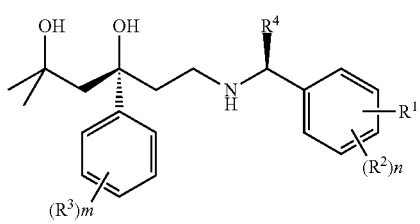

IV

In one embodiment ("the first method of making the compound of formula (IV)"), the method comprises allowing a compound of formula (III)

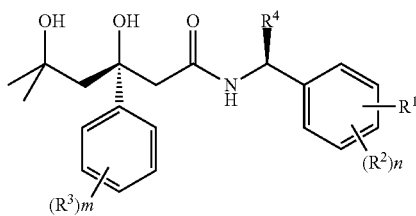

III to react with 1,1,3,3-tetramethyldisiloxane ([CH₃]₂SiH]₂O) in the presence of a transition metal catalyst to provide the compound of formula (IV), wherein m and n are each independently 0, 1 or 2;

R¹ is a leaving group selected from chloro, bromo, iodo, methoxy, arylsulfonyloxy and trifluoromethanesulfonyloxy; or R¹ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing R¹ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —(C₁-C₆)alkyl, —O(C₁-C₆)alkyl, and —(C₃-C₆)cycloalkyl; and wherein substituents for ring nitrogen atoms of said heterocyclic rings, when present, are selected from —(C₁-C₆)alkyl and —(C₃-C₆)cycloalkyl;

each R² and R³ is independently selected from —(C₁-C₆)alkyl, —O(C₁-C₆)alkyl, and —(C₃-C₆)cycloalkyl; wherein each of the —(C₁-C₆)alkyl, —O(C₁-C₆)alkyl, and —(C₃-C₆)cycloalkyl of said R² and R³ is optionally independently substituted with one to three R⁶ groups;

R⁴ is selected from —(C₁-C₆)alkyl and —(C₃-C₆)cycloalkyl; wherein the —(C₁-C₆)alkyl and —(C₃-C₆)cycloalkyl of said R⁴ is optionally substituted with one to three R⁶ groups; and each R⁶ is independently selected from halo, —(C₁-C₆)alkyl, —O(C₁-C₆)alkyl, and —(C₃-C₆)cycloalkyl.

In another embodiment, the invention relates to the first method of making the compound of formula (IV), wherein R¹ is bromo; and R⁴ is —(C₁-C₆)alkyl.

In another embodiment, the invention relates to the first method of making the compound of formula (IV), wherein m and n are each 0.

In another embodiment, the invention relates to the first method of making the compound of formula (IV) according to any of the embodiments above, wherein R⁴ is methyl.

In another embodiment, the invention relates to the first method of making the compound of formula (IV) according to the broadest embodiment above, wherein R¹ is bromo; R⁴ is —(C₁-C₆)alkyl; and m and n are each 0.

In another embodiment, the invention relates to the first method of making the compound of formula (IV) according to the embodiment immediately above, wherein R⁴ is methyl.

In another embodiment, the invention relates to the first method of making the compound of formula (IV) as described in the broadest embodiment above, wherein R¹ is oxodihydropyrid-4-yl; and wherein said nitrogen atom of said oxodihydropyrid-4-yl is substituted by methyl or cyclohexyl.

In another embodiment, the invention relates to the first method of making the compound of formula (IV) as described in the embodiment immediately above, wherein R¹ is oxodihydropyrid-4-yl and wherein said nitrogen atom of said oxodihydropyrid-4-yl is substituted by methyl or cyclohexyl; R⁴ is methyl; and m and n are each 0.

In another embodiment, the invention relates to the first method of making the compound of formula (II) according to any of the embodiments described above, wherein the transition metal catalyst is Ru₃(CO)₁₀.

In another embodiment ("the second method for making the compound of formula (IV)"), a method of making the compound of formula (IV) comprises allowing a compound formula (VIII):

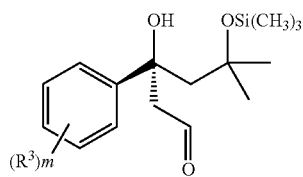

VIII to react with the compound of formula (IX)

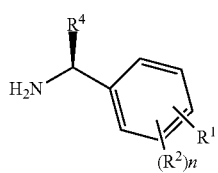

IX in the presence of a reducing agent to provide the compound of formula (III), wherein m and n are each independently 0, 1 or 2;

R¹ is a leaving group selected from chloro, bromo, iodo, methoxy, arylsulfonyloxy and trifluoromethanesulfonyloxy; or $R^1$ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing $R^1$ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —$(C_1-C_6)$alkyl, —$O(C_1-C_6)$alkyl, and —$(C_3-C_6)$cycloalkyl; and wherein substituents for ring nitrogen atoms of said heterocyclic rings, when present, are selected from —$(C_1-C_6)$alkyl and —$(C_3-C_6)$cycloalkyl;

each $R^2$ and $R^3$ is independently selected from —$(C_1-C_6)$alkyl, —$O(C_1-C_6)$alkyl, and —$(C_3-C_6)$cycloalkyl; wherein each of the —$(C_1-C_6)$alkyl, —$O(C_1-C_6)$alkyl, and —$(C_3-C_6)$cycloalkyl of said $R^2$ and $R^3$ is optionally independently substituted with one to three $R^6$ groups;

$R^4$ is selected from —$(C_1-C_6)$alkyl and —$(C_3-C_6)$cycloalkyl; wherein the —$(C_1-C_6)$alkyl and —$(C_3-C_6)$cycloalkyl of said $R^4$ is optionally substituted with one to three $R^6$ groups; and each $R^6$ is independently selected from halo, —$(C_1-C_6)$alkyl, —$O(C_1-C_6)$alkyl, and —$(C_3-C_6)$cycloalkyl.

In another embodiment, the invention relates to the second process for making the compound of formula (IV), wherein $R^1$ is bromo; and $R^4$ is —$(C_1-C_6)$alkyl;

In another embodiment, the invention relates to the second process for making the compound of formula (IV) according to any of the embodiments above, wherein m and n are each 0.

In another embodiment, the invention relates to the second process for making the compound of formula (IV) according to any of the embodiments above, wherein $R^4$ is methyl.

In another embodiment, the invention relates to the second process for making the compound of formula (IV) according to the broadest embodiment above, wherein $R^1$ is bromo; $R^4$ is —$(C_1-C_6)$alkyl; and m and n are each 0.

In another embodiment, the invention relates to the second process for making the compound of formula (IV) according to the embodiment immediately above, wherein $R^4$ is methyl.

In another embodiment, the invention relates to the second method of making the compound of formula (IV) as described in the broadest embodiment above, wherein $R^1$ is oxodihydropyrid-4-yl; and wherein said nitrogen atom of said oxodihydropyrid-4-yl is substituted by methyl or cyclohexyl.

In another embodiment, the invention relates to the second method of making the compound of formula (IV) as described in the embodiment immediately above, wherein $R^1$ is oxodihydropyrid-4-yl and wherein said nitrogen atom of said oxodihydropyrid-4-yl is substituted by methyl or cyclohexyl; $R^4$ is methyl; and m and n are each 0.

In another embodiment, the invention relates to the second process for making the compound of formula (IV) according to any of the embodiments above, wherein the reducing agent is sodium borohydride.

The invention still further relates to methods of making the compound of formula (III). In one embodiment, a method of making the compound of formula (III) comprises allowing a compound formula (VI):

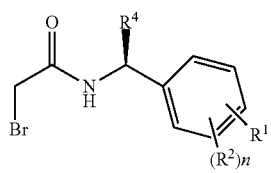

to react with a compound of formula (VII)

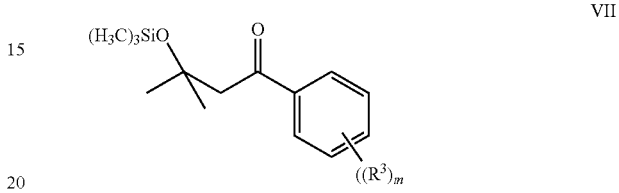

in the presence of a catalyst to provide the compound of formula (III), wherein m and n are each independently 0, 1 or 2;

$R^1$ is a leaving group selected from chloro, bromo, iodo, methoxy, arylsulfonyloxy and trifluoromethanesulfonyloxy; or $R^1$ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing $R^1$ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —$(C_1-C_6)$alkyl, —$O(C_1-C_6)$alkyl, and —$(C_3-C_6)$cycloalkyl; and wherein substituents for ring nitrogen atoms of said heterocyclic rings, when present, are selected from —$(C_1-C_6)$alkyl and —$(C_3-C_6)$cycloalkyl;

each $R^2$ and $R^3$ is independently selected from —$(C_1-C_6)$alkyl, —$O(C_1-C_6)$alkyl, and —$(C_3-C_6)$cycloalkyl; wherein each of the —$(C_1-C_6)$alkyl, —$O(C_1-C_6)$alkyl, and —$(C_3-C_6)$cycloalkyl of said $R^2$ and $R^3$ is optionally independently substituted with one to three $R^6$ groups;

$R^4$ is selected from —$(C_1-C_6)$alkyl and —$(C_3-C_6)$cycloalkyl; wherein the —$(C_1-C_6)$alkyl and —$(C_3-C_6)$cycloalkyl of said $R^4$ is optionally substituted with one to three $R^6$ groups; and each $R^6$ is independently selected from halo, —$(C_1-C_6)$alkyl, —$O(C_1-C_6)$alkyl, and —$(C_3-C_6)$cycloalkyl.

In another embodiment, the invention relates to a method of making the compound of formula (III) according to the broadest embodiment above, wherein $R^1$ is bromo; and $R^4$ is —$(C_1-C_6)$alkyl;

In another embodiment, the invention relates to a method of making the compound of formula (III) according to any of the embodiments above, wherein m and n are each 0.

In another embodiment, the invention relates to a method of making the compound of formula (III) according to any of the embodiments above, wherein $R^4$ is methyl.

In another embodiment, the invention relates to a method of making the compound of formula (III) according to the broadest embodiment above, wherein $R^1$ is bromo; $R^4$ is —$(C_1-C_6)$alkyl; and m and n are each 0.

In another embodiment, the invention relates to a method of making the compound of formula (III) according to the embodiment immediately above, wherein $R^4$ is methyl.

In another embodiment, the invention relates to a method of making the compound of formula (III) as described in the embodiment immediately above, wherein $R^1$ is oxodihydropyrid-4-yl and wherein said nitrogen atom of said oxodihydropyrid-4-yl is substituted by methyl or cyclohexyl; $R^4$ is methyl; and m and n are each 0.

In another embodiment, the invention relates to a method of making the compound of formula (III) according to any of the embodiments above, wherein the reducing agent is sodium borohydride.

In another embodiment, the invention relates to a method of making the compound of formula (III) according to any of the embodiments above, wherein the catalyst is $NiCl_2$dppe/ $Et_2Zn$.

In a further embodiment, the invention relates to a method of making the compound of formula (VIII)

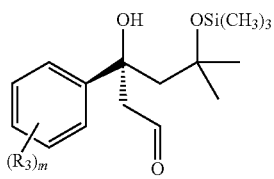

VIII comprising allowing a compound of formula (XII)

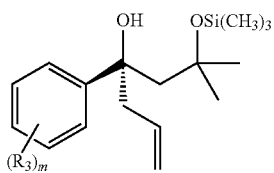

XII to react with ozone to provide the compound of formula (VIII), wherein
m is 0, 1 or 2;
each $R^3$ is independently selected from $—(C_1-C_6)$alkyl, $—O(C_1-C_6)$alkyl, and $—(C_3-C_6)$cycloalkyl; wherein each of the $—(C_1-C_6)$alkyl, $—O(C_1-C_6)$alkyl, and $—(C_3-C_6)$cycloalkyl of said $R^3$ is optionally independently substituted with one to three $R^6$ groups; and
each $R^6$ is independently selected from halo, $—(C_1-C_6)$alkyl, $—O(C_1-C_6)$alkyl, and $—(C_3-C_6)$cycloalkyl.

In another embodiment, the invention relates to a method for making the compound of formula (VIII), wherein m is 0.

In still a further embodiment, the invention relates to a method of making the compound of formula (XII):

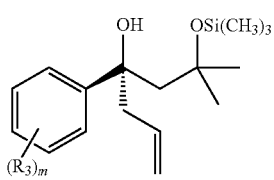

XII comprising allowing a compound of formula (VII)

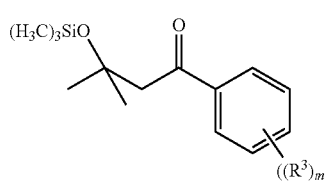

VII to react with 2-(2-propen-1-yl)-1,3,2-dioxaborinane in the presence of (R)-3,3'-dihalo-1,1'-binaphthyl-2,2'-diol to provide the compound of formula (XII), wherein
m is 0, 1 or 2;
each $R^3$ is independently selected from $—(C_1-C_6)$alkyl, $—O(C_1-C_6)$alkyl, and $—(C_3-C_6)$cycloalkyl; wherein each of the $—(C_1-C_6)$alkyl, $—O(C_1-C_6)$alkyl, and $—(C_3-C_6)$cycloalkyl of said $R^3$ is optionally independently substituted with one to three $R^6$ groups; and
each $R^6$ is independently selected from halo, $—(C_1-C_6)$alkyl, $—O(C_1-C_6)$alkyl, and $—(C_3-C_6)$cycloalkyl.

In another embodiment, the invention relates to a method for making the compound of formula (XII) according to any of the embodiments above, wherein m is 0.

In another embodiment, the invention relates to a method for making the compound of formula (XII) according to any of the embodiments above, wherein the (R)-3,3'-dihalo-1,1'-binaphthyl-2,2'-diol is selected from (R)-3,3'-difluoro-1,1'-binaphthyl-2,2'-diol, (R)-3,3'-dibromo-1,1'-binaphthyl-2,2'-diol and (R)-3,3'-dichloro-1,1'-binaphthyl-2,2'-diol.

In another embodiment, the invention relates to a method for making the compound of formula (XII) according to any of the embodiments above, wherein the (R)-3,3'-dihalo-1,1'-binaphthyl-2,2'-diol is (R)-3,3'-dibromo-1,1'-binaphthyl-2, 2'-diol.

In another embodiment, the invention relates to a method for making the compound of formula (XII) according to any of the embodiments above, wherein the (R)-3,3'-dihalo-1,1'-binaphthyl-2,2'-diol is (R)-3,3'-difluoro-1,1'-binaphthyl-2, 2'-diol.

In yet another embodiment, the invention relates to a compound of formula (II):

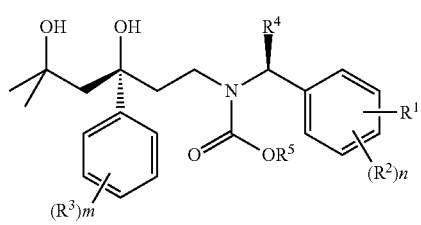

II wherein:
m and n are each independently 0, 1 or 2;
$R^1$ is selected from chloro, bromo, iodo, methoxy, arylsulfonyloxy and trifluoromethanesulfonyloxy;
each $R^2$ and $R^3$ is independently selected from $—(C_1-C_6)$alkyl, $—O(C_1-C_6)$alkyl, and $—(C_3-C_6)$cycloalkyl; wherein each of the $—(C_1-C_6)$alkyl, $—O(C_1-C_6)$alkyl, and $—(C_3-C_6)$cycloalkyl of said $R^2$ and $R^3$ is optionally independently substituted with one to three $R^6$ groups;
$R^4$ is selected from $—(C_1-C_6)$alkyl and $—(C_3-C_6)$cycloalkyl; wherein the $—(C_1-C_6)$alkyl and $—(C_3-C_6)$cycloalkyl of said $R^4$ is optionally substituted with one to three $R^6$ groups;

$R^5$ is selected from —($C_1$-$C_6$)alkyl, —($C_3$-$C_6$)cycloalkyl, and phenyl;

each $R^6$ is independently selected from halo, —($C_1$-$C_6$)alkyl, —O($C_1$-$C_6$)alkyl, and —($C_3$-$C_6$)cycloalkyl.

In another embodiment, the invention relates to a compound of formula (II), wherein $R^1$ is bromo; $R^4$ is —($C_1$-$C_6$) alkyl; $R^5$ is phenyl; and m and n are each 0.

In another embodiment, the invention relates to a compound of formula (II) as described in any of the embodiments above, wherein $R^1$ is bromo; $R^4$ is methyl, $R^5$ is phenyl; and m and n are each 0.

In yet another embodiment, the invention relates to a compound of formula (III):

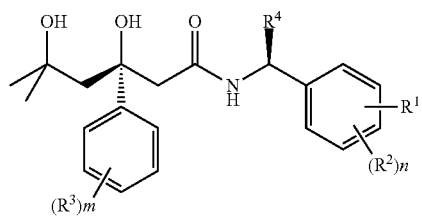

III wherein
m and n are each independently 0, 1 or 2;
$R^1$ is selected from chloro, bromo, iodo, methoxy, arylsulfonyloxy and trifluoromethanesulfonyloxy;
each $R^2$ and $R^3$ is independently selected from —($C_1$-$C_6$) alkyl, —O($C_1$-$C_6$)alkyl, and —($C_3$-$C_6$)cycloalkyl; wherein each of the —($C_1$-$C_6$)alkyl, —O($C_1$-$C_6$)alkyl, and —($C_3$-$C_6$) cycloalkyl of said $R^2$ and $R^3$ is optionally independently substituted with one to three $R^6$ groups;
$R^4$ is selected from —($C_1$-$C_6$)alkyl and —($C_3$-$C_6$)cycloalkyl; wherein the —($C_1$-$C_6$)alkyl and —($C_3$-$C_6$)cycloalkyl of said $R^4$ is optionally substituted with one to three $R^6$ groups; and each $R^6$ is independently selected from halo, —($C_1$-$C_6$)alkyl, —O($C_1$-$C_6$)alkyl, and —($C_3$-$C_6$)cycloalkyl.

In another embodiment, the invention relates to a compound of formula (III), wherein $R^1$ is bromo; $R^4$ is —($C_1$-$C_6$) alkyl; and m and n are each 0.

In another embodiment, the invention relates to a compound of formula (III) as described in any of the embodiments above, wherein $R^1$ is bromo; $R^4$ is methyl; and m and n are each 0.

In another embodiment, the invention relates to a compound of formula (IV):

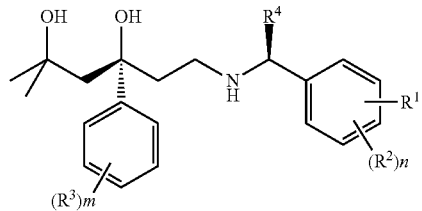

IV wherein:
m and n are each independently 0, 1 or 2;
$R^1$ is selected from chloro, bromo, iodo, methoxy, arylsulfonyloxy and trifluoromethanesulfonyloxy;
each $R^2$ and $R^3$ is independently selected from —($C_1$-$C_6$) alkyl, —O($C_1$-$C_6$)alkyl, and —($C_3$-$C_6$)cycloalkyl; wherein each of the —($C_1$-$C_6$)alkyl, —O($C_1$-$C_6$)alkyl, and —($C_3$-$C_6$) cycloalkyl of said $R^2$ and $R^3$ is optionally independently substituted with one to three $R^6$ groups;
$R^4$ is selected from —($C_1$-$C_6$)alkyl and —($C_3$-$C_6$)cycloalkyl; wherein the —($C_1$-$C_6$)alkyl and —($C_3$-$C_6$)cycloalkyl of said $R^4$ is optionally substituted with one to three $R^6$ groups; and each $R^6$ is independently selected from halo, —($C_1$-$C_6$)alkyl, —O($C_1$-$C_6$)alkyl, and —($C_3$-$C_6$)cycloalkyl.

In another embodiment, the invention relates to a compound of formula (IV), wherein $R^1$ is bromo; $R^4$ is —($C_1$-$C_6$) alkyl; and m and n are each 0.

In another embodiment, the invention relates to a compound of formula (IV) as described in any of the embodiments above, wherein $R^1$ is bromo; $R^4$ is methyl; and m and n are each 0.

In another embodiment, the invention relates to (R)-2,2'-bis(methoxymethoxy)-1,1'-binaphthyl.

Further aspects of the invention are described below.

DETAILED DESCRIPTION OF THE INVENTION

Abbreviations:
(R)-DBBINOL=(R)-3,3'-dibromo-1,1'-binaphthyl-2,2'-diol
n-BuLi=n-butyl lithium
t-BuOH=t-butanol
DIBAL-H=diisobutylaluminum hydride
DME=1,2-dimethoxyethane
DMF=dimethylformamide
EtOAc=ethyl acetate
i-$Pr_2$NH=diisopropylamine
LDA=lithium diisopropylamide
MeOH=methanol
MOMCl=chloro(methoxy)methane
MTBE=methyl tert-butyl ether
NFSI=N-fluoro-N-(phenylsulfonyl)benzenesulfonamide
NMP=N-methyl-2-pyrrolidone
THF=tetrahydrofuran
TMSCl=trimethylchlorosilane The term "($C_1$-$C_6$)alkyl" refers to branched and unbranched alkyl groups having from 1 to 6 carbon atoms. Examples of —($C_1$-$C_6$)alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the ($C_1$-$C_6$)alkyl group can be the point of attachment to another group or moiety.

The term "($C_3$-$C_6$)cycloalkyl" refers to a nonaromatic 3- to 6-membered monocyclic carbocyclic radical. Examples of "($C_3$-$C_6$)cycloalkyls include cyclopropyl, cyclobutyl, cyclohexyl, cyclopentyl and cyclohexyl.

The term "halo" or "halogen" refers to fluoro, chloro, bromo or iodo.

As noted above, the subject invention relates to compounds of formulae (II), (III), and (IV). The subject invention also relates to methods of making the compounds of formulae (I), (II), (III), (IV), (VIII) and (XII). These compounds are useful as intermediates for making 1,3-disubstited oxazinan-2-one 11-β-HSD1 inhibitors. Thus, it is desirable to have improved methods for making these intermediates.

Scheme 1 below depicts an exemplary method for making the compounds of formulae (I), (II), and (IV) according the processes of the invention.

Scheme 1

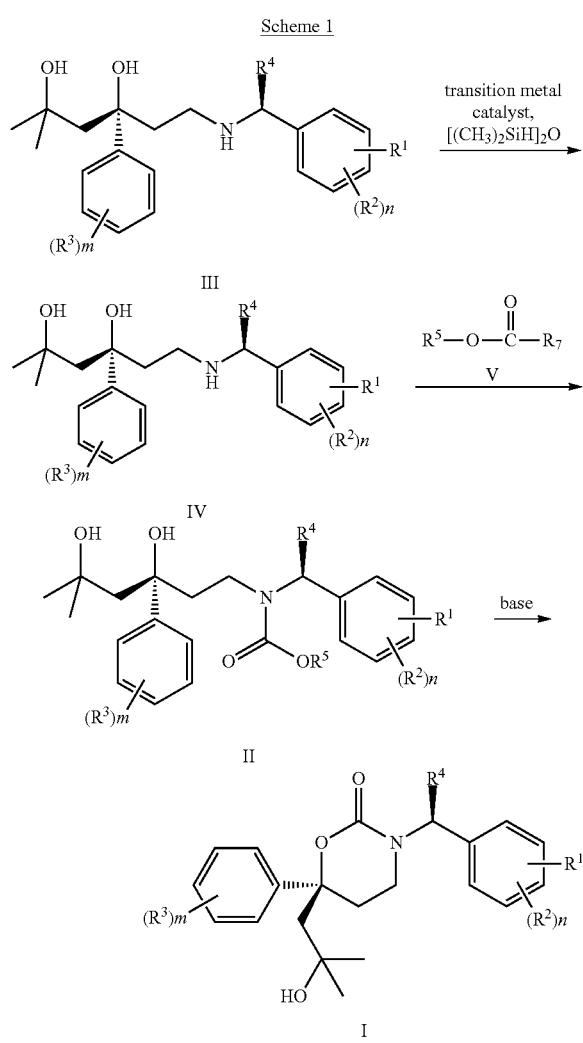

As depicted in Scheme 1, the compound of formula (I) can be prepared by allowing the compound of formula (II) to cyclize in the presence of base to provide the compound of formula (I). The cyclization can be carried out under aqueous or nonaqueous conditions. Nonlimiting examples of bases useful for carrying out the cyclization include aqueous bases comprising LiOH, NaOH, KOH, and CsOH. Nonlimiting examples of bases useful for carrying out the cyclization under non-aqueous conditions include KO-t-Bu, KO-t-pentyl, NaOMe, NaOEt, KOMe, KOEt, LiN(SiMe$_3$)$_2$, NaN(SiMe$_3$)$_2$, KN(SiMe$_3$)$_2$, and NaH. The cyclization may be carried out at a temperature of from about 2° C. to about 100° C.; typically about 25° C.

As depicted in Scheme 1, the compound of formula (II) can be prepared by allowing the compound of formula (III) to react with a reducing agent, e.g., 1,1,3,3-tetramethyldisiloxane, in the presence of a transition metal catalyst, e.g., Ru$_3$(CO)$_{10}$, to provide a compound of formula (IV). The compound of formula (IV) is then allowed to react with the compound of formula (V) to provide the compound of formula (II). Typically, the compound of formula (IV) is not isolated prior to carrying out the reaction with the compound of formula (V). Alternatively, the compound of formula (II) can be prepared by methods described in WO2010089303 which provide a mixture of diastereomers of the compound of formula (II). The compound of formula (II) can then be isolated from the mixture of diastereomers using known methods, e.g., recrystallization and/or chromatography (e.g., chiral chromatography).

The compounds of formula (I) where R$^1$ is a carbocyclic or heterocyclic ring as defined above are useful as 11-β-HSD1 inhibitors. Alternatively, compounds of formula (I) where R$^1$ is a leaving group as defined above are useful intermediates for making 11-β-HSD1 inhibitors. For example, the compound of formula (I) where R$^1$ is a leaving group can be reacted with a Grignard reagent of formula RMgBr (where R is a carbocyclic or heterocyclic ring as defined for R$^1$ above) to provide a 11-β-HSD1 inhibitor of formula (I) useful as an 11-β-HSD1 inhibitor (see, e.g., WO/2009/134400 and WO/2010/010150).

Schemes 2 and 3 below depict exemplary methods for making the compound of formula (III) according to the first process and second process of the invention.

Scheme 2 below depicts an exemplary first process for making the compound of formula (III) according to the invention.

Scheme 2

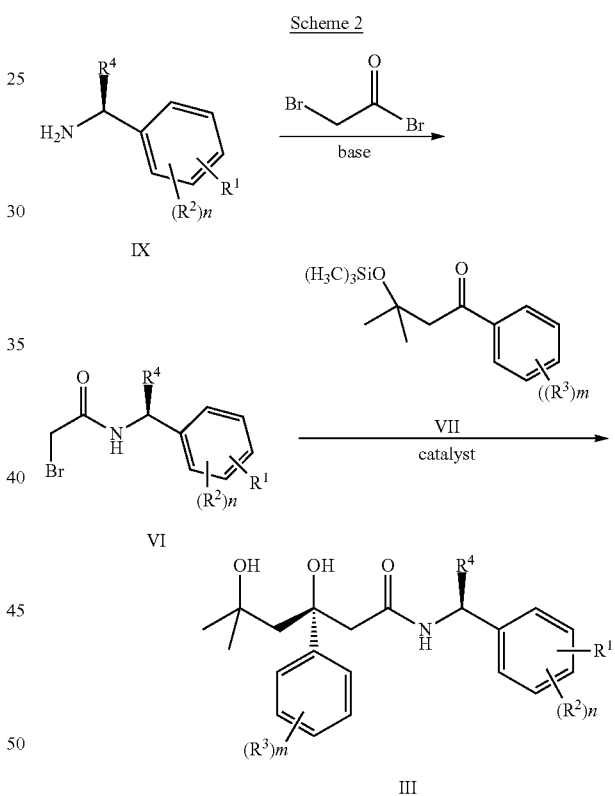

As shown in Scheme 2, the compound of formula (IX) is allowed to react with bromoacetyl bromide in the presence of base to provide the compound of formula (VI).

The compound of formula (VI) is then allowed to react with the compound of formula (VII) in the presence of a catalyst (e.g., NiCl$_2$dppe/Et$_2$Zn) at reduced temperature (e.g., about −4° C.) to provide the compound of formula (III). Compounds of formula (IX) are commercially available or can be made by known methods. Preferably the compound of formula (IX) is enantiomerically pure, i.e., the enantiomer depicted in Scheme 2 is present in at least about 90%, more preferably 95%; most preferably at least about 99%, based on the total amount of both enantiomers of the compound of formula (IX).

The compound of formula (III) can also be prepared using methods analogous to those described in, e.g., Devant, R. et al., *Chemische Berichte* 119: 2191-207 (1986). The compound of formula (VII) can also be made by known methods (see Odenkirk et al, *Tetrahedron Lett.* 1992, 33, 5729; Le Roux et al. *Synlett* 1998, 11, 1249; Chancharunee et al. *Tetrahedron Lett.* 2003, 44, 5683) or by the method depicted below in Scheme 2a using the procedure of Schneider et al, *Chem. Eur. J.* 2005, 11, 3010-3021.

Scheme 2a

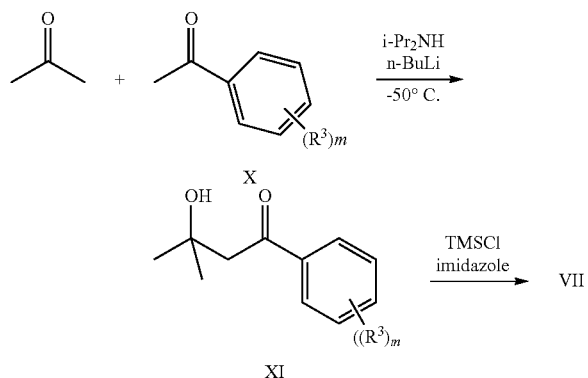

As depicted in Scheme 2a, a compound of formula (X) is allowed to react with acetone and n-BuLi in the presence of an amine (e.g., diisopropylamine) at reduced temperature. The compound of formula (XI) may also be prepared under milder conditions (e.g., 0° C.) using the procedure of Mukaiyama et al, *Organic Syntheses*, 1987, 65, 6.

Scheme 3 below depicts an exemplary method for making the compound of formula (III) according to the second process of the invention.

Scheme 3

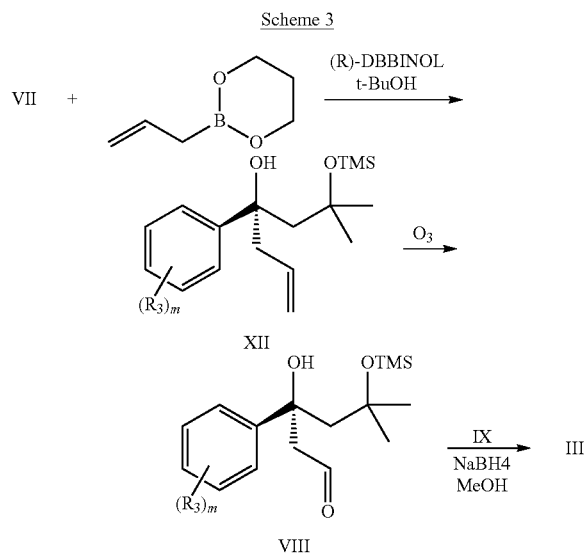

As depicted in Scheme 3, the compound of formula (VII) is allowed to react with 2-(2-propen-1-yl)-1,3,2-dioxaborinane in the presence of a biaryl catalyst such as (R)-3,3'-dibromo-1,1'-binaphthyl-2,2'-diol ((R)-DBBINOL), (R)-3,3'-dichloro-1,1'-binaphthyl-2,2'-diol or (R)-3,3'-difluoro-1,1'-binaphthyl-2,2'-diol and 2 equivalents of tertiary alcohol such as t-BuOH and t-amyl alcohol to provide the compound of formula (XII). The compound of formula (XII) is then subject to ozonolysis to provide the compound of formula (VIII) which is further allowed to undergo reductive amination with the compound of formula (IX) in the presence of reducing agent (e.g., $NaBH_4$) in alcoholic solvent to provide the compound of formula (III). 2-(2-propen-1-yl)-1,3,2-dioxaborinane can be prepared by the method described below in the Examples section or literature methods (see e.g., D. S. Barnett et al., *Angewandte Chemie, International Edition*, 48: 8679-8682 (2009) and H. C. Brown et al., *Journal of Organic Chemistry*, 55: 1868-74 (1990)).

(R)-3,3'-dibromo-1,1'-binaphthyl-2,2'-diol ((R)-DBBINOL) and (R)-3,3'-dichloro-1,1'-binaphthyl-2,2'-diol can be prepared by known methods (see, e.g., Ooi et al., *J. Am Chem. Soc.* 125(17): 5139-5151 (2003) and Egami et al., *J. Am Chem. Soc.* 131(17): 6082-6083 ((2009)). (R)-3,3'-difluoro-1,1'-binaphthyl-2,2'-diol can be prepared by the method described below in the Examples section.

Preferably the compound of formula (IX) used in Schemes 2 and 3 is enantiomerically pure, i.e., the enantiomer depicted in Schemes 2 and 3 is present in at least about 90%, more preferably 95%; most preferably at least about 99%, based on the total amount of both enantiomers of the compound of formula (IX). Applicants found that when using an enantiomerically pure form of (IX) as reagent, that chiral center of the diastereomeric products is fixed at the start of the reaction. The other chiral center of the diastereomeric compounds is determined by the process conditions described above and in the Examples. Thus, products formed by this process substantially comprise only two diastereomers. This allows for easier purification of product and improved overall yield.

EXAMPLES

General Procedures

The purity of the compounds described in the Examples section is determined using high performance liquid chromatography (HPLC) and nuclear magnetic resonance (NMR) spectroscopy. Reverse phase HPLC is used to determine the amount of each diastereomer present and the ratio of these amounts is used to determine the chiral purity of the diastereomeric product.

[1]NMR spectra are recorded on a 400 MHz Bruker spectrometer using d-6 DMSO as the sample solvent.

Example 1

Preparation of (S)-3-((S)-1-(4-bromophenyl)ethyl)-6-(2-hydroxy-2-methylpropyl)-6-phenyl-1,3-oxazinan-2-one (6)

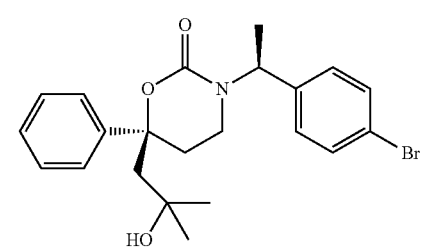

Step 1. Preparation of (S)-2-bromo-N-(1-(4-bromophenyl)ethyl)acetamide (1)

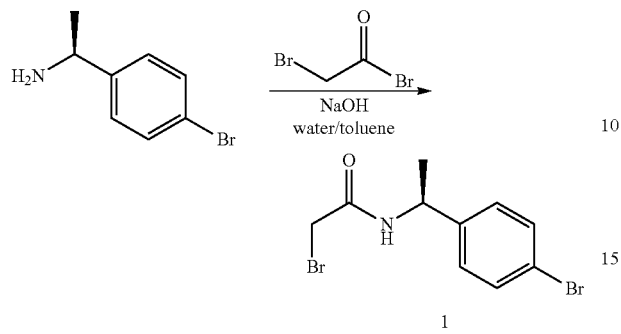

A solution of (S)-(4-bromophenyl)ethylamine (100.0 g, 0.50 mol; >99% chiral purity) and toluene (500 mL) is treated with a solution of NaOH (30.0 g, 0.75 mol) in water (500 mL). The resultant mixture is cooled to about 5° C. and treated with bromoacetyl bromide (52.2 mL, 0.60 mol). The reaction mixture is allowed to warm to about 25° C. over 1 hour. The solid is filtered and washed with water and heptane. The solid is then dried under vacuum at about 55° C. for 18 hours to provide 1 as a white solid. Yield: 156.4 g, 95.6%.

Step 2. Preparation of 3-methyl-1-phenyl-3-(trimethylsilyloxy)butan-1-one (2)

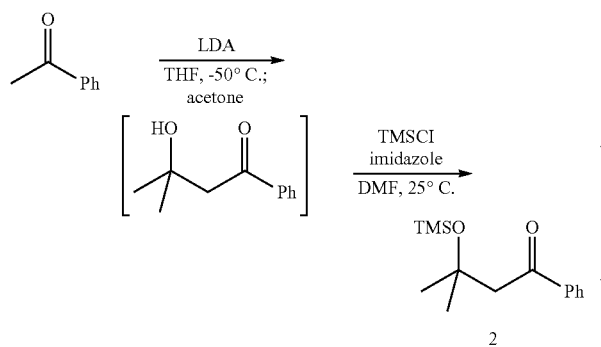

A flask is charged with THF (1 L), cooled to −50° C., and treated with lithium diisopropylamide (LDA) (1.05 L, 1.89 mol, 1.1 equiv, 1.8M in THF/heptane/ethylbenzene). The reactor contents are then treated with acetophenone (200 mL, 1.71 mol, 1.0 equiv) at a rate to maintain the batch at about −50° C. The reaction mixture is stirred at about −50° C. for 30 minutes then treated with acetone (151 mL, 2.06 mol, 1.2 equiv) at a rate to maintain the mixture at about −50° C. The reaction mixture is stirred at about −50° C. for 1 hour then treated with water (1 L) and heptane (500 mL). The reaction mixture is allowed to warm to 25° C., and the resultant organic phase is collected and washed with water (400 mL). The organic phase is concentrated to an oil and treated with a solution of imidazole (233.4 g, 3.43 mol, 2.0 equiv) and DMF (600 mL). The resultant solution is treated with chlorotrimethylsilane (217.6 mL, 1.71 mol, 1.0 equiv) at a rate to maintain the reaction mixture at no more than 35° C. The reaction mixture is stirred at 25° C. for 1 hour, and diluted with heptane (600 mL) and water (1 L). The resultant organic phase is collected, washed with water (3×500 mL), and concentrated. The resultant oil is then vacuum distilled at 1-3 mm Hg (product distills at 83-88° C.) to provide 2 as a yellow liquid. Yield: 160.3 g, 37%.

Step 3. Preparation of (R)—N—((S)-1-(4-bromophenyl)ethyl)-3,5-dihydroxy-5-methyl-3-phenylhexanamide (3)

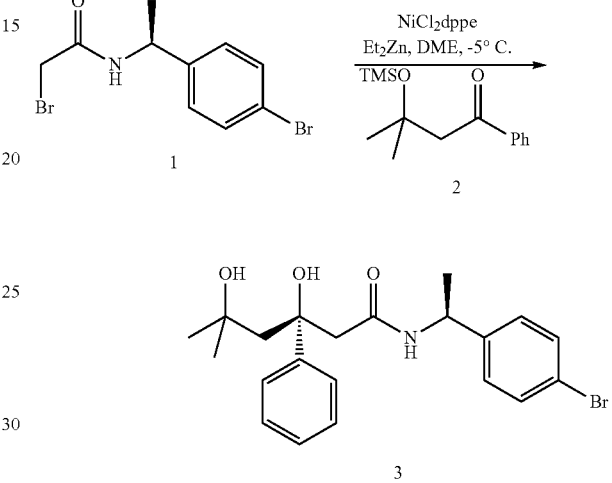

A flask is charged with 1 (120.0 g, 0.366 mol), 2 (120.0 g, 0.479 mol) and NiCl$_2$(dppe) (1.93 g, 3.66 mmol). The flask is purged with nitrogen and charged with DME (240 mL). The resultant slurry is cooled to about −20° C. and treated with diethylzinc (30 wt. % solution in toluene, 477 mL, 1.097 mol) at a rate to keep the temperature of the reaction mixture between −15 to −5° C. The reaction mixture is then stirred at −5 to 0° C. for 2 hours, treated with 6N aqueous HCl (600 mL), and stirred for 15 minutes. The reaction mixture is treated with isopropyl acetate (120 mL), stirred at 25° C. for 30 minutes, cooled to 10° C., and held at 10° C. for 30 minutes. The resultant solids are collected by filtration, and washed with water, toluene, and heptane. The solid is then dried at 70° C. for 18 hours to provide 3 as a white solid. Yield: 98.3 g, 62.1%; 97.1 wt. % purity. Diastereomeric ratio: 98.9:1.1. Melting point: 150-152° C. LC-MS: 419.8/421.8 (100%, 95%); calculated exact mass: 419.1.

Step 4. Preparation of (S)-6-((S)-1-(4-bromophenyl)ethylamino)-2-methyl-4-phenylhexane-2,4-diol (4)

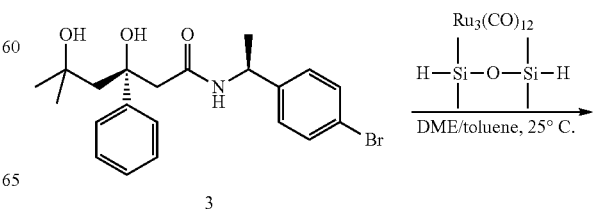

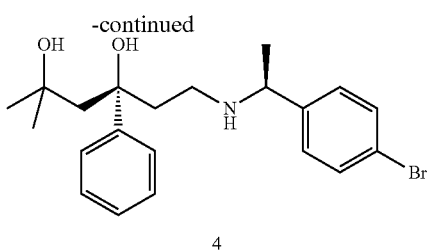

4

A flask is charged with 3 (15.0 g, 96.5 wt. %, 34.4 mmol) and Ru₃(CO)₁₂ (220 mg, 0.344 mmol). The flask is purged with nitrogen and charged with toluene (45 mL) and DME (15 mL). The reaction mixture is then treated with 1,1,3,3-tetramethyldisiloxane (24.3 mL, 137.7 mmol). The reaction mixture is stirred at 25° C. for 24-36 hours, treated with 1.5N aqueous HCl (30 mL), and stirred for 2 hours. The reaction mixture is then treated with 2N aqueous NaOH (30 mL) and stirred for 30 minutes to provide 4. LC-MS: 403.8/405.8 (85%, 100%); calculated exact mass: 405.1. The reaction mixture was used in Step 5 below without further treatment.

Step 5. Preparation of phenyl (S)-1-(4-bromophenyl) ethyl((S)-3,5-dihydroxy-5-methyl-3-phenylhexyl) carbamate (5)

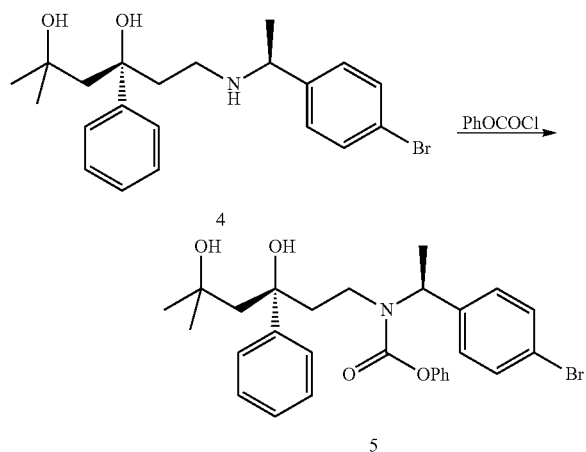

Preparation 1: Compound 5 was first prepared by cooling a reaction mixture prepared according to Step 4 above to about 10° C. and treating it drop-wise with phenyl chloroformate (1.25 molar equivalents based on the molar amount of compound 3 used in Step 4). The reaction mixture is stirred at 20-25° C. for 2-18 hours, extracted with EtOAc, and the organic extract washed with 3N aqueous HCl. The combined organic phases are distilled to remove EtOAc and DME. The resultant solution is treated with heptane (30 mL), cooled to about 5° C., and held at about 5° C. for 3 hours. The resultant solids are collected by filtration, washed with heptane, and dried under vacuum at 25° C. for 18 hours to provide 5 as an off-white solid.

Preparation 2: Using a procedure similar to that described in Preparation 1 above, the reaction mixture from Step 4 above is cooled to about 10° C. and treated drop-wise with phenyl chloroformate (5.2 mL, 41.3 mmol). The reaction mixture is stirred at 20-25° C. for 2-18 hours, extracted with EtOAc, and the organic extract washed with 3N aqueous HCl.

The combined organic phases are distilled to remove EtOAc and DME. The resultant solution is treated with heptane (30 mL), cooled to about 5° C., seeded with 5 (obtained from Preparation 1 immediately above), and held at about 5° C. for 3 hours. The resultant solids are collected by filtration, washed with heptane, and dried under vacuum at 25° C. for 18 hours to provide 5 as an off-white solid. Yield: 14.61 g, 78.3%; 97.2% purity by weight. Melting point: 129-131° C. LC-MS: 507.6/509.6 (95%, 100%); [M−H2O]+; calculated exact mass for M−H2O: 507.1.

Step 6. Synthesis of (S)-3-((S)-1-(4-bromophenyl) ethyl)-6-(2-hydroxy-2-methylpropyl)-6-phenyl-1,3-oxazinan-2-one (6)

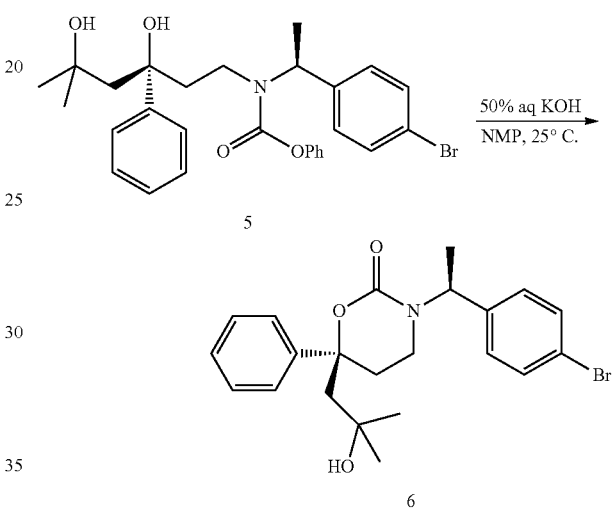

A flask is charged with phenyl (S)-1-(4-bromophenyl) ethyl((S)-3,5-dihydroxy-5-methyl-3-phenylhexyl)carbamate (25.0 g, 47.5 mmol) and NMP (125 mL). The resultant solution is treated with 50 wt. % aqueous KOH (12.5 mL), stirred at 25° C. for 1 hour, and treated with water (250 mL). The resultant slurry is stirred at 25° C. for 1 hour, and the solids collected by filtration. The solids are then washed with water and heptane, and dried under vacuum at 50° C. for 18 hours to provide 6 as a white solid. Yield: 19.7 g, 95.1%; 99.1%. purity by weight.

Example 2

Example 2 describes an alternative preparation of (S)-6-((S)-1-(4-bromophenyl)ethylamino)-2-methyl-4-phenylhexane-2,4-diol (4) described in Step 4 of Example 1 above.

Step 1. Synthesis of 2-allyl-1,3,2-dioxaborinane (7)

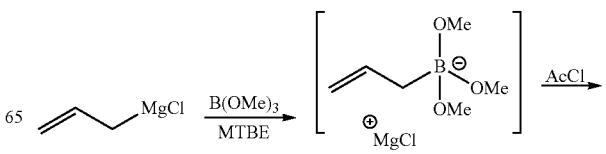

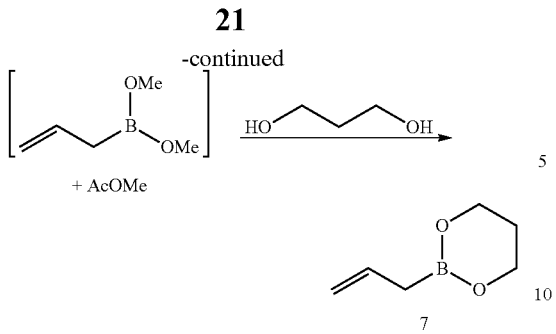

A reactor is purged with N₂ and charged with 2M allylmagnesium chloride in THF (850 mL, 1.7 mol), anhydrous THF (755.7 g, 850 mL, 10.48 mol) and methyl-t-butyl ether (629.0 g, 850 mL, 7.1 mol), cooled to −65° C., and treated with trimethylboronate (176.7 g, 1.7 mol) while maintaining a temperature of less than −60° C. The resultant milky solution is maintained at −55 to −60° C. for 30 minutes and slowly warmed to 0° C. over 30 minutes. The mixture is then treated with acetyl chloride (120.1 g, 1.53 mol) while maintaining a temperature of less than 5° C. The mixture is allowed to slowly warm to about 20° C. over 30 minutes and treated with 1,3-propanediol (116.4 g, 1.53 mol). The reaction mixture is maintained at about 20° C. for 6 hours, concentrated to about ⅓ of its original volume under reduced pressure at a temperature of less than about 29° C., and treated with MTBE (580 mL) and heptane (720 ml). The resultant mixture is again reduced to about ⅓ of its original volume under reduced pressure, filtered through Celite, and the Celite plug rinsed with MTBE (3.5 L). The combined filtrates are then concentrated under reduced pressure at 29° C. to provide 7 as a colorless oil. Yield: 193 g; 75% based on 1,3-propanediol. The product was further purified by vacuum distillation prior to use in Step 2.

Step 2. Synthesis of (S)-6-methyl-4-phenyl-6-(trimethylsilyloxy)hept-1-en-4-ol (8)

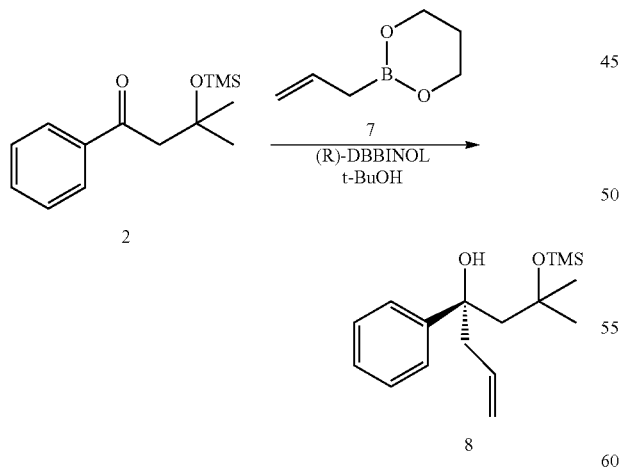

A flask is charged with 2 (4.1 g; 16.5 mmol) (see Step 2 of Example 1 above), 17 mol % of (R)-DBBINOL (1.3 g; 2.9 mmol), and 2.4 eq. of t-BuOH (2.9 g; 39.1 mmol) under nitrogen atmosphere. The reaction mixture is then treated with 7 (3.7 g; 29.4 mmol) from Step 1 above at 23° C. and stirred for about 24 hours. The mixture is treated with water (50 mL), hexanes (50 mL), 3M HCl (1 mL), and stirred for 1 hour. The resultant organic layer is collected and washed with water (20 mL), 1M NaOH (2×10 mL), and water (2×10 mL). The organic layer is then concentrated to provide 8 as light yellow oil. Yield: 4.8 g, 16.99 mmol, 99% (>99% ee).

Step 3. Synthesis of Synthesis of (R)-3-hydroxy-5-methyl-3-phenyl-5-(trimethylsilyloxy)hexanal (9)

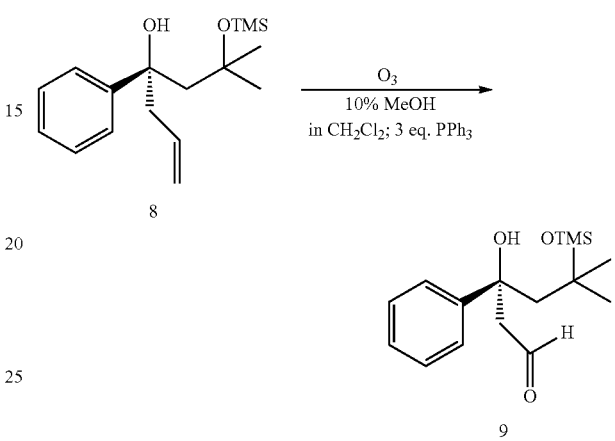

Ozone is bubbled through a solution of 8 (0.5 g) in 10% MeOH/CH₂Cl₂ (20 mL) at −70 to −78° C. until a blue color persists. O₂ is then bubbled through the solution for 10 min followed by N₂ bubbling for 5 min. The solution is then treated with triphenylphosphine (Ph₃P) and warmed to 22° C. The mixture is concentrated, purified on silica gel (Combiflash; eluent: 5% EtOAc in hexane), and concentrated to provide 9 as clear colorless oil. Yield: 0.35 g, 1.18 mmol; 93%.

Step 4. Synthesis of (S)-6-((S)-1-(4-bromophenyl)ethylamino)-2-methyl-4-phenylhexane-2,4-diol (4)

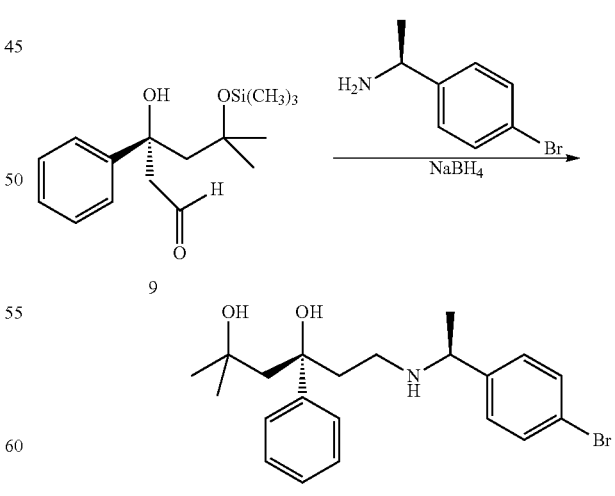

A solution of 9 (20 mg; 0.068 mmol) in CH₃OH (1.0 mL) at 23° C. is treated with (S)-(4-bromophenyl)ethylamine (15 mg; 0.075 mmol; >99% chiral purity). The reaction mixture is then treated with solid NaBH$_4$ (3.85 mg; 0.1 mmol), stirred overnight, and treated with 1M HCl (2 mL), and basified with 1 M NaOH (10 mL). The mixture is extracted with EtOAc (10 mL), and the organic extracts washed with saturated aqueous NaCl (10 mL). The washed extracts are then concentrated to provide 4 as an oil. Yield: 26 mg, 0.063 mmol, 95%.

Example 3

Preparation of (R)-3,3'-difluoro-1,1'-binaphthyl-2,2'-diol (10)

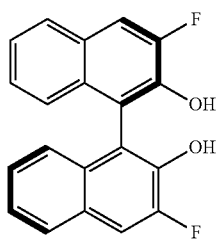

Step 1: Synthesis of (R)-2,2'-bis(methoxymethoxy)-1,1'-binaphthyl (11)

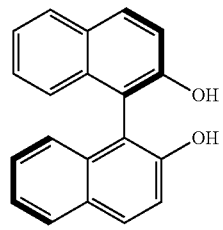

A solution of (R)-1,1'-binaphthyl-2,2'-diol (30 g, 0.10 mol) in THF (200 ml) is added to a stirred slurry of 60 wt % NaH (10.48 g, 0.26 mol) in THF (100 mL) at 0-10° C. The mixture is stirred for 1 hour and treated with chloro(methoxy)methane (MOMCl) (20.25 g, 0.25 mol) while maintaining the temperature below 10° C. The resultant mixture is stirred for 1 hour at 0-5° C. then treated with water (100 mL) to quench the reaction. The organic phase is collected and the aqueous phase extracted with EtOAc (2×250 mL). The combined organics layers are washed with water (200 mL) and concentrated. The resultant pale yellow solid is then slurried in 10:1 (vol/vol) hexane/EtOAc. The solids are collected by filtration and dried under reduced pressure top provide 11. Yield: 38.5 g, 98%.

Step 2: Synthesis of (R)-3,3'-difluoro-2,2'-bis(methoxymethoxy)-1,1'-binaphthyl (12)

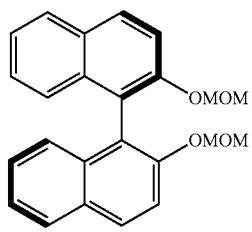

A solution of n-BuLi (1.6M, 30.46 mL, 48.7 mL) in hexane is added to a stirred solution of 11 in Et$_2$O (400 mL) at 23° C. After 3 hour the resultant slurry is cooled to 0° C., treated with THF (40 mL), mixed for 0.5 hour, and treated with a solution of N-fluoro-N-(phenylsulfonyl)benzenesulfonamide (NFSI) (15.5 g, 49.2 mmol) in THF (40 mL). After 10 minutes the reaction is quenched with water, and the organic layer is collected. The aqueous layer is extracted with EtOAc (2×100 mL), and the combined organic layer is washed with water (100 mL) and concentrated. The resultant residue is redissolved in a minimum volume of toluene, added to a silica gel column, eluted with hexane/EtOAc, and concentrated to provide 10 as a white solid to provide 12. Yield: 6.3 g, 77%.

Step 3: Synthesis (R)-3,3'-difluoro-1,1'-binaphthyl-2,2'-diol (10)

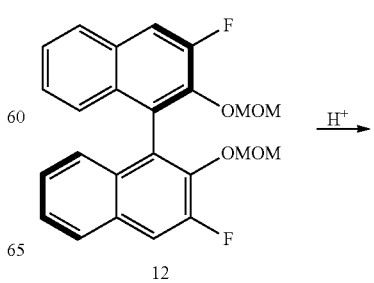

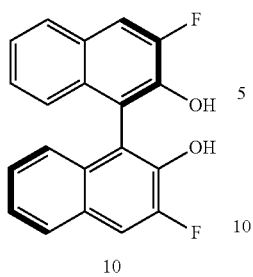

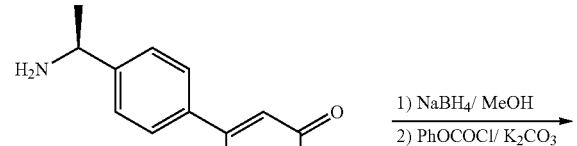

Amberlyst® 15 (Aldrich) 15 (6 g) is added to a stirred solution of 12 (5.6 g, 13.7 mmol) in 1:1 THF/MeOH (vol/vol) (60 mL). The resultant mixture is heated at reflux for 3 hours then allowed to cool to about 25° C. The mixture is then filtered through a Celite pad, and the filtrate is concentrated. The resultant residue is redissolved in a minimum volume of toluene, added to a silica gel column, eluted with hexane/EtOAc, and concentrated to provide 10 as a white solid. Yield: 4.3 g, 97%. $^1$H NMR (500 MHz, CDCl$_3$): δ 7.79 (d, 2H, J=8.2 Hz), 7.65 (d, 2H, J=11.2 Hz), 7.36 (t, 2H, J=7.4 Hz), 7.22 (t, 2H, J=7.9 Hz), 7.10 (d, 2H, J=8.5 Hz), 5.96 (s, 2H). MS: 323 (M+H).

Example 4

(S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one (13)

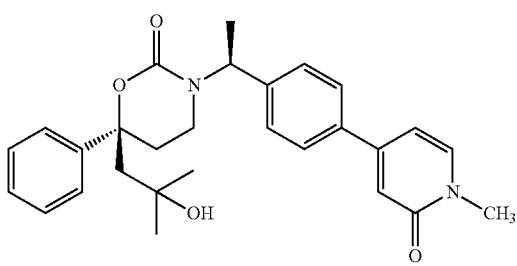

13

Step 1: Preparation of phenyl (S)-3,5-dihydroxy-5-methyl-3-phenylhexyl((S)-1-(4-(1-methyl-2-oxo-1,2-dihydropyridin-4-yl)phenyl)ethyl)carbamate (14)

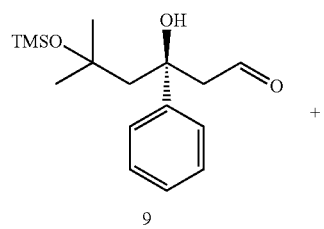

9

NaBH$_4$ (0.226 g, 5.97 mmol) is added in portions to a mixture of 9 (1.17 g, 3.98 mmol) and (S)-4-(4-(1-aminoethyl)phenyl)-1-methylpyridin-2(1H)-one (15) (1.00 g, 4.37 g) in MeOH (5 mL). The mixture is stirred at 25° C. for 15 h, then treated with K$_2$CO$_3$ (1.65 g, 11.93 mmol) followed by phenyl chloroformate (0.93, 5.97 mmol). The resultant suspension is then stirred at 25° C. for 1 hour, treated with water (15 mL) over 30 min, and stirred at 25° C. for 2 hours. The solids are collected by filtration, rinsed with MeOH/water (⅓, 20 mL), and dried to provide 14 as off-white solid. Yield: 1.76 g, 79.8%. $^1$H NMR (DMSO-d$_6$, 500 MHz): δ 7.77 (d, J=7.2 Hz, 1H), 7.66 (m, 2H), 7.46-7.00 (m, 12H), 6.67 (d, J=2.1 Hz, 1H), 6.56 (dd, J=7.0, 2.1 Hz, 1H), 5.82 (s, 1H), 5.28 (br s, 1H), 5.11 (s, 1H), 3.45 (s, 3H), 3.35 (m, 1H), 2.59 (m, 1H), 2.14-1.81 (m, 4H), 1.55-1.29 (m, 3H), 1.01 (s, 3H), 0.61 (s, 3H); $^{13}$C NMR (DMSO-d$_6$, 400 MHz): δ 161.97, 154.08, 151.20, 150.09, 147.53, 142.31, 139.85, 135.59, 129.18, 127.59, 127.40, 126.66, 125.87, 125.35, 125.07, 121.77, 114.79, 103.75, 75.53, 71.48, 53.82, 51.19, 44.90, 36.36, 32.80, 29.22, 21.58, 17.00; LC-MS (ES): m/z 555 (M+H), 479 (100).

Step 2. Preparation of (S)-6-(2-hydroxy-2-methyl-propyl)-3-((S)-1-(4-(1-methyl-2-oxo-1,2-dihydropy-ridin-4-yl)phenyl)ethyl)-6-phenyl-1,3-oxazinan-2-one (13)

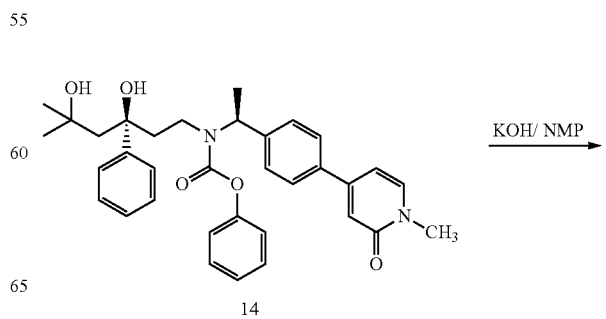

14

-continued

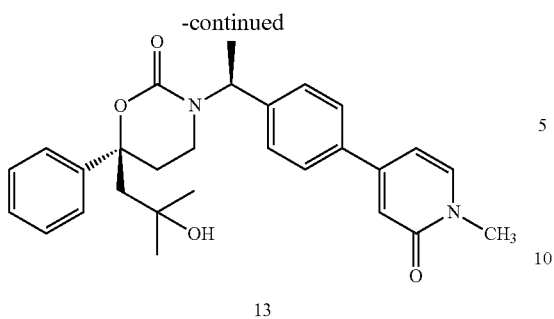

13

A solution of 25% KOH in MeOH (1.21 g, 5.41 mmol) is added to a solution of 14 (1.00 g, 1.80 mmol) in 1-methylpyrrolidin-2-one (NMP, 4 mL). The resultant mixture is stirred at about 25° C. for 15 h, treated with water (15 mL), and stirred at 25° C. for 0.5 h. The resultant solids are collected via filtration, rinsed with MeOH/water (⅓, 20 mL), and dried to provide 13 as white solid. Yield: 0.68 g, 81.4%. Purity: 99.6 area % at 220 nm. $^1$H NMR (DMSO-d$_6$, 500 MHz): δ 7.74 (d, J=7.1 Hz, 1H), 7.43 (d, J=7.7 Hz, 2H), 7.34 (m, 5H), 6.95 (d, J=7.7 Hz, 2H), 6.56 (s, 1H), 6.47 (d, J=6.0 Hz, 1H), 5.43 (m, 1H), 4.26 (s, 1H), 3.43 (s, 3H, 3.33 (s, 2H), 3.02 (m, 1H), 2.43 (m, 1H), 2.14 (m, 1H), 2.02 (s, 2H), 1.46 (d, J=6.8 Hz, 3H), 1.18 (s, 3H), 0.87 (s, 3H); $^{13}$C NMR (DMSO-d$_6$, 400 MHz): δ 161.93, 152.44, 150.05, 143.37, 141.24, 139.85, 135.32, 128.33, 127.22, 127.10, 126.26, 124.90, 114.68, 103.70, 83.04, 69.30, 54.01, 52.62, 36.35, 36.22, 31.51, 30.81, 29.91, 15.46.

What is claimed is:

1. A method of making a compound of formula (I):

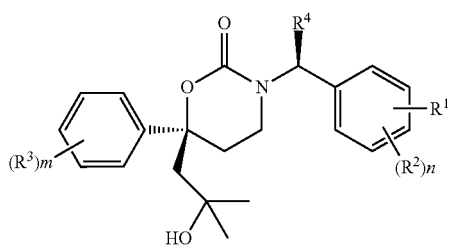

I comprising allowing a compound of formula (II):

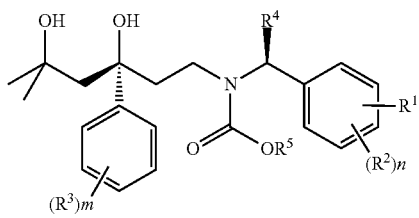

II to react in the presence of base to form the compound of formula (I), wherein:

m and n are each independently 0, 1 or 2;

$R^1$ is a leaving group selected from chloro, bromo, iodo, methoxy, arylsulfonyloxy and trifluoromethanesulfonyloxy; or $R^1$ is a carbocyclic or heterocyclic ring selected from phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, pyridazinyl, pyrimidinyl, pyrazinyl, benzimidazolyl, benztriazolyl, oxodihydropyridyl, oxodihydropyridazinyl, oxodihydropyrimidinyl and oxodihydropyrazinyl; wherein each of the foregoing $R^1$ carbocyclic or heterocyclic rings may be optionally substituted by 1 to 4 groups; wherein substituents for ring carbon atoms of said carbocyclic or heterocyclic rings are independently selected from halogen, cyano, oxo, nitro, —($C_1$-$C_6$)alkyl, —O($C_1$-$C_6$)alkyl, and —($C_3$-$C_6$)cycloalkyl; and wherein substituents for ring nitrogen atoms of said heterocyclic rings, when present, are selected from —($C_1$-$C_6$)alkyl and —($C_3$-$C_6$)cycloalkyl;

each $R^2$ and $R^3$ is independently selected from —($C_1$-$C_6$)alkyl, —O($C_1$-$C_6$)alkyl, and —($C_3$-$C_6$)cycloalkyl; wherein each of the —($C_1$-$C_6$)alkyl, —O($C_1$-$C_6$)alkyl, and —($C_3$-$C_6$)cycloalkyl of said $R^2$ and $R^3$ is optionally independently substituted with one to three $R^6$ groups;

$R^4$ is selected from —($C_1$-$C_6$)alkyl and —($C_3$-$C_6$)cycloalkyl; wherein the —($C_1$-$C_6$)alkyl and —($C_3$-$C_6$)cycloalkyl of said $R^4$ is optionally substituted with one to three $R^6$ groups;

$R^5$ is selected from —($C_1$-$C_6$)alkyl, —($C_3$-$C_6$)cycloalkyl, and phenyl; and each $R^6$ is independently selected from halo, —($C_1$-$C_6$)alkyl, —O($C_1$-$C_6$)alkyl, and —($C_3$-$C_6$)cycloalkyl.

2. The method of claim 1, wherein $R^1$ is bromo; and $R^4$ is —($C_1$-$C_6$)alkyl.

3. The method of claim 1, wherein m and n are each 0.

4. The method of claim 1, wherein $R^4$ is methyl.

5. The method of claim 1, wherein $R^5$ is phenyl.

6. The method of claim 1, wherein $R^1$ is oxodihydropyrid-4-yl; and wherein said nitrogen atom of said oxodihydropyrid-4-yl is substituted by methyl or cyclohexyl.

* * * * *